United States Patent [19]
Orban et al.

[11] 3,959,295
[45] May 25, 1976

[54] PROCESS FOR THE PREPARATION OF 2,2,6,6-TETRAMETHYL-4-OXOPIPERIDINE

[75] Inventors: Ivan Orban, Basel; Hanns Lind, Liestal; Heimo Brunetti, Reinach; Jean Rody, Basel; Michael Rasberger, Allschwil, all of Switzerland

[73] Assignee: Ciba-Geigy Corporation, Ardsley, N.Y.

[22] Filed: June 21, 1974

[21] Appl. No.: 481,922

[30] Foreign Application Priority Data

June 25, 1973   Switzerland...................... 9241/73
Oct. 5, 1973    Switzerland...................... 14257/73
Apr. 24, 1974   Switzerland...................... 5599/73
May 22, 1974    Switzerland...................... 7018/73

[52] U.S. Cl. ............................................ 260/293.89
[51] Int. Cl.² ........................................ C07D 211/74
[58] Field of Search ............................ 260/293.89

[56] References Cited
UNITED STATES PATENTS
3,513,170   5/1970   Murayama et al.............. 260/294.7

OTHER PUBLICATIONS
Chem. Abstracts, 70:114968x, (1969).

*Primary Examiner*—G. Thomas Todd
*Attorney, Agent, or Firm*—Nestor W. Shust

[57] ABSTRACT

2,2,6,6-Tetramethyl-4-oxopiperidine is prepared from acetone and ammonia in the presence of acidic catalysts. Suitable catalysts are Lewis acids, protionic acids and their salts with ammonia or with organic bases, as for example $BF_3$, $NH_4Cl$ or $H_2SO_4$. The addition of an alcohol such as methanol as well as the use of a cocatalyst may promote the reaction. The process may be carried out in two steps, in the first of which the temperature is held below 35°C. In the second step a further amount of acetone is added and the temperature is rised to about 40° to 65°C.

53 Claims, No Drawings

PROCESS FOR THE PREPARATION OF 2,2,6,6-TETRAMETHYL-4-OXOPIPERIDINE

The preparation of 2,2,6,6-tetramethyl-4-oxopiperidine is already known. It comprises the reaction of 2,2,4,4,6-pentamethyl-2,3,4,5-tetrahydropyrimidine with a Lewis acid, preferably zinc chloride or calcium chloride, in the presence of water. This pyrimidine derivative, usable as starting material, can be prepared from acetone and ammonia; its isolation from the reaction medium and, optionally, purification involve, however, an appreciable amount of work.

Attempts have also been made to combine both reaction steps, i.e. to prepare 2,2,6,6-tetramethyl-4-oxopiperidine directly from acetone, without isolation of pentamethyltetrahydropyrimidine. The relevant tests have hitherto not produced satisfactory yields: reaction mixtures are formed of which the separation is difficult and inefficient.

It has now been found that, surprisingly, it is possible, under specific processing conditions, to obtain 2,2,6,6-tetramethyl-4-oxopiperidine directly from acetone with a good yield and in a high degree of purity. The process comprises two stages, which can be performed one immediately after the other, so that it is particularly suitable for the large-scale commercial manufacture of tetramethylpiperidone. The process according to the invention is characterised in that a. acetone is reacted with ammonia in the presence of 0.2 to 12 mol-%, relative to the acetone used, of an acid catalyst at 5° to 60°C, and b. the reaction is completed, with or without the addition of further acetone, by further heating, with the total amount of acetone used in the reaction being with respect to the employed amount of ammonia in a molar ratio equal to or greater than 1.6 : 1.

In the first stage of the process, preferably at least 0.15 mol of ammonia is allowed to react with the acetone; however, for practical reasons it is more advantageous to saturate the reaction mixture with ammonia: an excess of ammonia is therefore preferred.

The catalyst used can be either a Lewis acid, such as, e.g. aluminium chloride, tin tetrachloride or — preferably — boron trifluoride or a boron trifluoride adduct; or a proton acid, or the salt of a proton acid with ammonia or with a nitrogen-containing organic base, particularly a primary, secondary or tertiary nitrogen base.

Examples of such proton acids or of acid components in salts used as acid catalysts are, in particular: mineral acids such as hydrochloric acid, hydrobromic acid, hydriodic acid, nitric acid, sulphuric acid and phosphoric acid, as well as sulphonic acids such as aliphatic or aromatic sulphonic acids, e.g. methanesulphonic acid, benzenesulphonic acid, p-toluenesulphonic acid or naphthalenesulphonic acid, phosphonic acids and phosphinic acids such as aliphatic or aromatic ones, e.g. methyl-, benzyl- or phenylphosphonic acid, or dimethyl-, diethyl- or phenylphosphinic acid, and carboxylic acids such as monobasic, dibasic or tri-basic aliphatic or aromatic carboxylic acids, e.g. saturated or unsaturated monobasic aliphatic carboxylic acids having 1–18 carbon atoms, such as formic acid, acetic acid, chloroacetic acid, dichloroacetic acid, trichloroacetic acid, propionic acid, butyric acid, lauric acid, palmitic acid, stearic acid, acrylic acid, methacrylic acid and cinnamic acid, saturated and unsaturated, dibasic aliphatic carboxylic acids, such as oxalic acid, malonic acid, succinic acid, adipic acid, sebacic acid, tartaric acid, malic acid, fumaric acid and maleic acid, tribasic aliphatic carboxylic acids such as citric acid, monobasic aromatic carboxylic acids such as optionally substituted benzoic acid and naphthoic acid, and dibasic aromatic carboxylic acids such as phthalic acid and terephthalic acid. Those preferred are monobasic and dibasic aliphatic or aromatic carboxylic acids and monobasic aromatic sulphonic acids such as acetic acid, succinic acid, maleic acid, benzoic acid, o-iodobenzoic acid, m-methylbenzoic acid, p-tert.-butylbenzoic acid, p-toluenesulphonic acid and cinnamic acid. Suitable organic bases are: aliphatic, alicyclic and aromatic, primary, secondary and tertiary amines, saturated and unsaturated nitrogen bases, urea, thiourea and basic ion exchange resins. They are thus aliphatic, primary amines, e.g. methylamine, ethylamine, n-butylamine, octylamine, dodecylamine and hexamethylene-diamine, aliphatic secondary amines, e.g. dimethylamine, diethylamine, di-n-propylamine and di-isobutylamine, aliphatic tertiary amines, e.g. triethylamine, alicyclic primary amines, e.g. cyclohexylamine, aromatic primary amines, e.g. aniline, toluidine, naphthylamine and benzidine, aromatic secondary amines, e.g. N-methylaniline and diphenylamine, aromatic tertiary amines, e.g. N,N-diethylaniline, saturated and unsaturated nitrogen bases, e.g. heterocyclic bases, e.g. pyrrolidine, piperidine, N-methyl-2-pyrrolidone, pyrazolidine, piperazine, pyridine, picoline, indoline, quinuclidine, morpholine, N-methylmorpholine, 1,4-diazabicyclo[2,2,2]-octane and triacetoneamine, urea, thiourea and strongly and weakly basic ion exchange resins. Also preferred are acetonine and diacetoneamine and triacetoneamine. Examples of preferred salts are: cyclohexylamine-formiate, pyridine-formiate, pyridine-p-toluenesulphonate, di-n-butylamine-acetate, di-n-butylamine-benzoate, morpholine-succinate, morpholine-maleate, triethylamine-acetate, triethylamine-succinate, triethylamine-maleate, aniline-acetate, triacetoneamine-p-toluenesulphonate and acetonine hydrochloride.

Particularly preferred is ammonium chloride or boron trifluoride, or a mixture of both compounds.

These catalysts are used in an amount of 0.2 to 12 mol-%, relative to the acetone used; the amount preferably employed is 2–5 mol-%.

As additional co-catalyst, it is possible to use: potassium iodide, sodium iodide, lithium bromide, lithium iodide, lithium rhodanide, ammonium rhodanide, lithium cyanide, lithium nitrate, ammonium sulphide, bromine, iodine, or a bromide, iodide, nitrate, methanesulphonate, benzenesulphonate or p-toluenesulphonate of ammonia, triethylamine, urea or thiourea; for example, in amounts of 0.01 to 0.5 mol-%, relative to acetone.

The reaction temperature in the first stage of the process is 5° to 60°C, preferably 5° to 35°C, particularly preferably 5° to 25°C. In the first stage of the process, an addition of a mono- or polyfunctional alcohol proves advantageous. Examples of alcohols suitable for the purpose are: methanol, butanol, cyclohexanol, benzyl alcohol, ethylene glycol, diethylene glycol, propylene glycol, ethylene glycol monoethyl ether or 2-ethylhexanol. It is preferable to use lower monoalcohols such as methanol, ethanol and isopropanol, among which methanol is especially preferred.

The reaction time of this first stage of the process, occurring at low temperature, is at least 1 hour, preferably 3 hours.

A variant of the process is as follows:

Subsequent to this first part of the process, an addition is made to the reaction medium of a further amount of acetone and/or diacetone alcohol or mesityl oxide or phorone or diacetoneamine or triacetoneamine, and the temperature is raised, preferably to 40° to 65°C. In the usual case, acetone is added, the amount being at least 0.5 part, particularly more than 1 part, preferably 2–4 parts, per part of the initially used amount of acetone. Besides acetone, the above mentioned acetone derivatives may be used, preferably diacetone alcohol or a mixture thereof with acetone. Furthermore, it can be of advantage in this second stage of the process to add a further amount of catalyst. This can occur together with the addition of acetone or acetone derivative, or it can occur somewhat later. Suitable catalysts in this case are the same substances as in the first stage of the process; especially suitable are boron trifluoride, ammonium chloride, concentrated sulphuric acid and hydrogen chloride.

The reaction time required for the second stage, occurring at elevated temperature, is about 3 to 20 hours.

Also the following procedure is advantageous for stage (b): 8–20 hours at 50°–55°C, or firstly 2–7 hours at 50°–55°C and then a further 2–6 hours at reflux temperature, particularly at about 56°–60°C.

In both stages of the process, it is possible to operate under pressure, e.g. at 1–30, especially at 1–10, and more particularly at 1–3 atmospheres excess pressure. Temperatures of more than 60°C are possible in this case.

The isolation of tetramethylpiperidone can be effected in a manner known per se; for example, by the addition of water and separation as hydrate, or by the addition of acid, such as hydrochloric acid, sulphuric acid or oxalic acid, and separation as salt, or by the addition of an excess of liquor, especially concentrated liquor, such as sodium hydroxide solution or potassium hydroxide solution, and separation as organic layer, or particularly by distillation, optionally after neutralisation of the catalyst by addition of a base, such as sodium hydroxide, potassium hydroxide or sodium carbonate.

The acetone used in the first stage of the process can contain to a certain extent water and/or condensation products of acetone, such as diacetone alcohol, mesityl oxide, phorone, diacetoneamine and/or triacetonediamine. Such an addition can have a favourable effect on the yield. A preferred condensation product of acetone is mesityl oxide and particularly diacetone alcohol. It is thus possible to use the distillate obtained on distillative processing at the end of the second stage as raw material in the first stage, which results in a high acetone conversion. If the water content in the reaction medium increases too much, e.g. in the case of such a re-cyclisation, then it is recommended that a part of the water be removed from the reaction mixture. This can be effected, for example, by adding to the reaction mixture, at the end of the first stage, concentrated alkali, e.g. sodium hydroxide solution, and, after a brief stirring, separating the aqueous layer.

Also organic solvents can be used in the process according to the invention. Organic solvents particularly suitable for the process according to the invention are, e.g.: hydrocarbons such as aromatic hydrocarbons, e.g. benzene, toluene and xylene, as well as aliphatic hydrocarbons such as hexane, heptane and cyclohexane, also chlorinated hydrocarbons such as methylene chloride, trichloroethane, carbon tetrachloride, chloroform, ethylene chloride and chlorobenzene, as well as ethers such as tetrahydrofuran, dioxane and diethyl ether, and nitriles such as acetonitrile, and aprotic polar solvents such as sulpholane, nitromethane, dimethylformamide, dimethylacetamide, tetramethylurea, hexamethylphosphoric acid amide and dimethylsulphoxide, and, particularly preferred, alcohols such as mono- or polyfunctional, unsubstituted or substituted aliphatic alcohols, e.g. lower alkanols such as methanol, ethanol, propanol, iso-propanol and tert.-butanol, as well as cyclohexanol, benzyl alcohol, ethylene glycol monomethyl ether, ethylene glycol and propane-1,3-diol, especially a $C_1$–$C_4$-alcohol such as methanol, and diacetone alcohol, phorone, diacetoneamine, triacetonediamine and mesityl oxide. Also mixtures of the above solvents are equally suitable.

The present invention is illustrated by the following examples. Further advantageous arrangements of the process according to the invention are to be seen from the claims.

EXAMPLE 1

A suspension consisting of 11 g of ammonium chloride and a mixture of 340 g of acetone and 64 g of methanol is saturated in the course of 12 hours at 13° to 17°C with ammonia gas. The resulting colourless oil is subsequently diluted with 350 g of acetone, and maintained, with stirring, for 15 to 20 hours at 50°–55°C. Excess solvent is thereupon removed by evaporation in vacuo, and 36 g of water is added to the reddish residue. The crystallisation occurring at 0° to 5°C is completed by 2 hours' stirring. The result is 286 g of 2,2,6,6-tetramethyl-4-oxopiperidine hydrate, M.P. 55°–60°C, in the form of slightly yellowish coloured crystals.

The product is obtained as oxalate salt, decomposition point 180°C, if the reaction mixture is neutralised with oxalic acid.

EXAMPLE 2

The procedure as described in Example 1 is followed except that in the second stage there is added, together with the addition of acetone, 1.3 g of boron trifluoride dissolved in ether. The isolation of 2,2,6,6-tetramethyl-4-oxopiperidine is performed as given in Example 1.

EXAMPLE 3

The procedure followed is as described in Example 1 except that, instead of ammonium chloride, 1.3 g of boron trifluoride dissolved in ether is used. In the second stage of the process, an addition is then made to the reaction mixture of 11 g of ammonium chloride together with the acetone.

EXAMPLES 4–7

A suspension consisting of 11 g of ammonium chloride, 340 g of acetone and 64 g of methanol is saturated in the course of 4 hours at 13° to 17°C with ammonia gas. The resulting colourless oil is subsequently diluted with 900 g of acetone, and maintained, with stirring, for 15 to 20 hours at 50°–55°C. After the first 6 hours, an addition is made dropwise to the solution, within 1–2 hours of 70 g of 97% sulphuric acid. At the end of the reaction period, the pH-value of the reaction mixture is adjusted with 97% sulphuric acid within 1–2 hours to the value 4.5 to 5. The formed suspension of the hydrosulphate of 2,2,6,6-tetramethyl-4-oxopiperidine is filtered at 5°–10°C and then washed with acetone. The yield is 655 g of hydrosulphate salt, which corresponds to 381 g of 2,2,6,6-tetramethyl-4-oxopiperidine.

If the same procedure as described above is carried out with the exception however that in the second stage the amount of acetone and sulphuric acid given in Table 1 is used, then the yields shown in the third column of the table are obtained.

Table 1

| Example | Acetone amount in 2nd stage | Sulphuric acid amount (added after 6 hours) | Yield of 2,2,6,6-tetra-methyl-4-oxo-piperidine 100% (isolated as hydrosulphate) |
|---|---|---|---|
| 5 | 900 g | — | 342 g |
| 6 | 1140 g | 70 g | 402 g |
| 7 | 670 g | 45 g | 314 g |

EXAMPLE 8

A suspension consisting of 11 g of ammonium chloride, 340 g of acetone and 64 g of methanol is saturated in the course of 4 hours at 13° to 17°C with ammonia gas. The resulting colourless oil is subsequently diluted with 900 g of acetone, and the whole is maintained, with stirring, for 15 to 20 hours at 50°–55°C. After the first 6 hours, the pH-value of the solution is adjusted to 8.5–8.6 by the introduction of about 23 g of hydrogen chloride gas. At the end of the reaction period, the pH-value of the reaction mixture is adjusted with hydrogen chloride within 1–2 hours to the value of 5 to 6. The formed suspension of the hydrochloride of 2,2,6,6-tetramethyl-4-oxopiperidine is filtered at 0°–5°C and subsequently washed with acetone. The yield is 400 g of hydrochloride salt, which corresponds to 293 g of 2,2,6,6-tetramethyl-4-oxopiperidine.

There is isolated from the mother liquor, after removal by distillation of $H_2O$ and methanol and dilution of the distillation residue with acetone, a further 95 g of hydrochloride, which corresponds to 70 g of 2,2,6,6-tetramethyl-4-oxopiperidine.

EXAMPLE 9

40 g of ammonia gas is introduced in the course of about 4 hours at 13°–15°C into a mixture consisting of 126 g of acetone, 22.5 g of methanol and 4.7 g of ammonium chloride. The reaction mixture is subsequently stirred for a further 30 minutes at the same temperature. An addition is then made to the reaction mixture of 220 g of diacetone alcohol and 110 g of acetone; the whole is heated within 1 hour to 55°C and held at this temperature for 12 hours. Processing by fractional distillation yields 125 g of 2,2,6,6-tetramethyl-4-oxopiperidine.

EXAMPLE 10

A suspension consisting of 11 g of ammonium chloride, 340 g of acetone and 64 g of methanol is saturated in the course of 4 hours at 13° to 17°C with ammonia gas. The resulting colourless oil is subsequently diluted with 900 g of acetone, and maintained, with stirring, for 15 to 20 hours at 50°–55°C.

The reaction mixture obtained contains, according to gas-chromatography, 378 g of 2,2,6,6-tetramethyl-4-oxopiperidine (triacetoneamine), which is isolated by distillation.

EXAMPLE 11

A suspension of 11 g of ammonium chloride, 340 g of acetone and 4 g of an 20% aqueous solution of ammonium sulphide is saturated in the course of 4 hours at 13° to 17°C with ammonia gas. The procedure followed is then as described in Example 10.

The reaction mixture finally contains 450 g of triacetoneamine.

EXAMPLE 12

A suspension of 11 g of ammonium chloride, 340 g of acetone and 1 g of potassium iodide is saturated in the course of 4 hours with ammonia gas. The subsequent procedure is as described in Example 10. The reaction mixture contains 400 g of triacetoneamine.

EXAMPLE 13

The procedure is carried out as in Example 10 except that, instead of 64 g of methanol, 64 g of dioxane is used.

The reaction mixture contains 314 g of triacetoneamine.

EXAMPLE 14

The procedure followed is as described in Example 10 except that, instead of 64 g of methanol, 64 g of ethanol is used.

The reaction mixture contains 363 g of triacetoneamine.

EXAMPLE 15

The procedure followed is as described in Example 10 except that, instead of 64 g of methanol, 64 g of isopropanol is used.

The reaction mixture contains 350 g of triacetoneamine.

EXAMPLE 16

The same result as according to Example 15 is obtained if the methanol is replaced by 64 g of dimethylformamide.

EXAMPLE 17

The procedure is the same as given in Example 10 but without a methanol addition.

The reaction mixture contains 336 g of triacetoneamine.

EXAMPLE 18

A suspension consisting of 11 g of ammonium chloride, 340 g of acetone and 64 g of methanol is saturated in the course of 4 hours at 13° to 17°C with ammonia gas. The resulting colourless oil is subsequently diluted with 1360 g of acetone, and the whole is maintained, with stirring, for 15–20 hours at 50°–55°C.

The resulting reaction mixture contains 420 g of triacetoneamine.

EXAMPLE 19

The procedure followed is as described in Example 10 except that, after dilution with 900 g of acetone, the reaction mixture is firstly stirred for 6 hours at 50°–55°C and then for 3 hours with vigorous refluxing (at 56°–60°C).

The resulting reaction mixture contains 337 g of triacetoneamine.

EXAMPLE 20

The procedure followed is as described in Example 10 except that, instead of 11 g of ammonium chloride, 5.5 g and 38 g, respectively, of ammonium chloride are used.

| Ammonium chloride g | g of triacetoneamine in reaction mixture |
|---|---|
| 5.5 | 220 |
| 38 | 381 |

What we claim is:

1. Process for the preparation of 2,2,6,6-tetramethyl-4-oxopiperidine, wherein
   a. acetone is reacted with ammonia in the presence of 0.2–12 mol-%, relative to the acetone used, of an acid catalyst at 5°–60°C, and
   b. the reaction is completed, with or without the addition of further acetone, by further heating, with the total amount of acetone used in the reaction being with respect to the employed amount of ammonia in a molar ratio equal to or greater than 1.6 : 1.

2. Process according to claim 1, wherein the acetone in stage (a) of the process is partially replaced by diacetone alcohol and/or mesityl oxide.

3. Process according to claim 1, wherein the acetone in stage (b) of the process is partially or completely replaced by diacetone alcohol, mesityl oxide, phorone, diacetoneamine or triacetonediamine.

4. Process according to claim 2, wherein the acetone is partially replaced by mesityl oxide.

5. Process according to claim 3, wherein the acetone is partially or completely replaced by diacetone alcohol.

6. Process according to claim 1, wherein the total amount of acetone used in the reaction with respect to the employed amount of ammonia is in a molar ratio of 2–6 : 1.

7. Process according to claim 1, wherein, in stage (a) of the process, acetone and ammonia are used in a molar ratio of 0.8–1.1 : 1, and the remaining acetone is used in stage (b) of the process.

8. Process according to claim 1, wherein the employed acid catalyst is the salt of a proton acid with ammonia or with a nitrogen-containing organic base.

9. Process according to claim 8, wherein the employed proton acid is a mineral acid or an organic acid.

10. Process according to claim 9, wherein the employed organic acid is a sulphonic acid or a carboxylic acid.

11. Process according to claim 8, wherein the employed salt is the ammonium salt of a mineral acid.

12. Process according to claim 8, wherein the employed salt is the ammonium salt of an organic acid.

13. Process according to claim 8, wherein the employed salt is a mineral-acid salt of a nitrogen-containing organic base.

14. Process according to claim 8, wherein the employed salt is a salt of a nitrogen-containing organic base with an organic acid.

15. Process according to claim 8, wherein the employed nitrogen-containing organic base is triacetoneamine, trithylamine, hexamethylenediamine, 1,4-diazabicyclo [2,2,2]-octane, urea or thiourea.

16. Process according to claim 8, wherein there is used a salt of hydrochloric, hydrobromide or hydroiodic acid, of nitric acid, of an organic sulphonic acid, cyanoacetic acid or of a haloacetic acid.

17. Process according to claim 8, wherein there is used an ammonium salt of hydrochloric acid, hydrobromic acid, hydriodic acid, nitric acid, benzenesulphonic acid, p-toluenesulphonic acid, methanesulphonic acid, dichloro- or cyanoacetic acid.

18. Process according to claim 8, wherein there is used a salt of hydrochloric acid, hydrobromic acid, hydriodic acid, nitric acid, benzenesulphonic acid, p-toluenesulphonic acid, methanesulphonic acid, dichloroacetic acid or cyanoacetic acid with triacetoneamine, triethylamine, hexamethylenediamine, 1,4-diazabicyclo[2,2,2-octane, urea or thiourea.

19. Process according to claim 8, wherein the salt used is ammonium chloride, ammonium bromide, ammonium iodide, ammonium formiate, ammonium tosylate, urea nitrate, urea tosylate, hexamethylenediamine-dihydrochloride or triacetoneamine-hydrochloride.

20. Process according to claim 8, wherein there is used hexamethylene-dihydrochloride.

21. Process according to claim 1, wherein the employed acid catalyst is an acid.

22. Process according to claim 21, wherein the employed acid is a Lewis acid.

23. Process according to claim 22, wherein boron trifluoride is used.

24. Process according to claim 21, wherein the employed acid is a proton acid.

25. Process according to claim 24, wherein the employed proton acid is a mineral acid or an organic acid.

26. Process according to claim 25, wherein the employed organic acid is a sulphonic acid or a carboxylic acid.

27. Process according to claim 24, wherein the employed proton acid is hydrochloric acid, formic acid, acetic acid, malonic acid, succinic acid, maleic acid, benzoic acid, cinnamic acid, benzenesulphonic acid or p-toluenesulphonic acid.

28. Process according to claim 1, wherein there is used, in addition to the acid catalyst, 0.01 to 0.5 mol-%, relative to the acetone used in stage (a) of the process, of a co-catalyst different from the said catalyst.

29. Process according to claim 28, wherein the employed co-catalyst is potassium iodide, sodium iodide, lithium bromide, lithium iodide, lithium rhodanide, ammonium rhodanide, lithium cyanide, lithium nitrate, ammonium sulphide, bromine, iodine or a bromide, iodide, nitrate, methanesulphonate, benzenesulphonate or p-toluenesulphonate of ammonia, triethylamine, urea or thiourea.

30. Process according to claim 1, wherein the reaction in stage (a) of the process is performed at a temperature of 5°–35°C.

31. Process according to claim 1, wherein the reaction in stage (a) of the process is performed at a temperature of 5°–25°C.

32. Process according to claim 1, wherein the reaction is performed in the presence of a mono- or polyfunctional alcohol or of mixtures of such alcohols.

33. Process according to claim 32, wherein the employed alcohol is a lower monoalcohol.

34. Process according to claim 33, wherein methanol, ethanol, ethylene glycol monomethyl ether or mixtures of thse solvents are used.

35. Process according to claim 33, wherein the employed alcohol is methanol.

36. Process according to claim 1, wherein there is used per mol of acetone at least 0.15 mol of ammonia.

37. Process according to claim 32, wherein
a. acetone is allowed to react, for at least 3 hours at a temperature of between 5° and 25°C, with at least 0.15 mol of ammonia per mol of acetone starting material in methanol or ethanol in the presence of 0.2 to 7 mol-%, relative to acetone as starting material,
   1. of an ammonium salt of an acid having a pK-value of below 5.0, or
   2. of the corresponding acid alone, or
   3. of boron trifluoride, or
   4. of boron trifluoride in admixture with the ammonium salt according to 1 or with the acid according to 2; and subsequently
b. at least half of the acetone used in stage (a) of the process is added, and the reaction is allowed to proceed at a temperature of between 40° and 65°C for at least 3 hours.

38. Process according to claim 37, wherein the catalyst employed in stage (a) of the process is ammonium chloride or boron trifluoride or a mixture of both.

39. Process according to claim 38, wherein
a. the acetone is saturated with ammonia gas, and the reaction is performed in methanol in the presence of 2–5 mol-%, relative to the acetone used, of ammonium chloride at a temperature of between 10° and 17°C for 3 to 5 hours; and
b. the reaction is continued at a temperature of between 50° and 55°C for 8 to 20 hours.

40. Process according to claim 1, wherein the acid catalyst used in stage (a) is a Lewis acid or proton acid and the reaction is performed at 5°–35°C; and in stage (b) the reaction is completed by addition of further acetone and/or diacetone alcohol, mesityl oxide, phorone, diacetoneamine or triacetoneamine and by increase of temperature.

41. Process according to claim 40, wherein there is used in stage (b) of the process an additional amount of a Lewis acid or of a proton acid.

42. Process according to claim 37, wherein there is used in stage (b) of the process an additional amount of a Lewis acid or of a proton acid.

43. Process according to claim 42, wherein boron trifluoride or ammonium chloride is added in stage (b) of the process.

44. Process according to claim 42, wherein concentrated sulphuric acid is added in stage (b) of the process.

45. Process according to claim 42, wherein hydrogen chloride is added in stage (b) of the process.

46. Process according to claim 40, wherein there is used in stage (b) of the process at least 0.5 part of acetone and/or diacetone alcohol or mesityl oxide per part of the acetone used in stage (a).

47. Process according to claim 46, wherein there is used in stage (b) of the process 2–4 parts of acetone and/or diacetone alcohol or mesityl oxide per part of the acetone used in stage (a).

48. Process according to claim 37, wherein there is used in stage (b) of the process the 2–4-fold amount of the acetone used in stage (a) of the process.

49. Process according to claim 37, wherein there are added in stage (b) of the process additionally at least double the amount of acetone used in stage (a) of the process, and 0.05 to 1 mol, calculated on the acetone used in stage (a) of the process, of 97% sulphuric acid, and the reaction is performed between temperatures of 40° and 65°C for 8 to 20 hours.

50. Process according to claim 49, wherein there is used, instead of sulphuric acid, hydrochloric acid in stage (b) of the process.

51. Process according to claim 48, wherein there are added in stage (b) of the process the 2–4-fold amount of the acetone used in stage (a) and 5–12 mol-%, relative to the acetone used in stage (a) of concentrated sulphuric acid or of hydrogen chloride, and the reaction is performed for 8–20 hours at 40° to 65°C.

52. Process according to claim 2, wherein the employed acetone contains water and/or lower monoalcohols.

53. Process according to claim 1, wherein the reaction is performed at over +5°C and under pressure.

* * * * *